United States Patent
Bonnet

(10) Patent No.: US 6,574,507 B1
(45) Date of Patent: Jun. 3, 2003

(54) ACTIVE IMPLANTABLE MEDICAL DEVICE FOR TREATING SLEEP APNEA SYNDROME BY ELECTROSTIMULATION

(75) Inventor: Jean-Luc Bonnet, Monrouge (FR)

(73) Assignee: Ela Medical S.A., Montrouge (FR)

( * ) Notice: Subject to any disclaimer, the term of this patent is extended or adjusted under 35 U.S.C. 154(b) by 0 days.

(21) Appl. No.: 09/508,068

(22) PCT Filed: Jul. 5, 1999

(86) PCT No.: PCT/IB99/01345
§ 371 (c)(1),
(2), (4) Date: Mar. 6, 2000

(87) PCT Pub. No.: WO00/01438
PCT Pub. Date: Jan. 13, 2000

(30) Foreign Application Priority Data

Jul. 6, 1998 (FR) .............................................. 98 08639

(51) Int. Cl.⁷ .............................................. A61N 1/365
(52) U.S. Cl. ........................................... 607/20; 607/42
(58) Field of Search ................................ 600/508, 509, 600/529, 547; 607/9, 11, 16, 17, 20, 119, 42

(56) References Cited

U.S. PATENT DOCUMENTS

| | | | |
|---|---|---|---|
| 4,580,575 A | * | 4/1986 | Birnbaum et al. |
| 4,730,618 A | * | 3/1988 | Lekholm et al. |
| 5,024,222 A | | 6/1991 | Thacker ................ 128/419 PG |
| 5,187,657 A | * | 2/1993 | Forbes |
| 5,201,808 A | * | 4/1993 | Steinhaus et al. |
| 5,318,597 A | * | 6/1994 | Hauck et al. |
| 5,485,851 A | | 1/1996 | Erickson ..................... 128/716 |
| 5,713,933 A | | 2/1998 | Condie et al. ................. 607/28 |
| 5,722,996 A | * | 3/1998 | Bonnet et al. |
| 5,766,228 A | * | 6/1998 | Bonnet et al. |
| 6,126,611 A | * | 10/2000 | Bourgeois et al. |
| 6,141,590 A | * | 10/2000 | Renirie et al. |

FOREIGN PATENT DOCUMENTS

| | | | |
|---|---|---|---|
| EP | 0 750 920 | 1/1997 | .......... A61N/1/365 |
| EP | 0 770 407 | 5/1997 | .......... A61N/1/365 |
| WO | WO 84 02080 | 6/1984 | .......... A61M/15/00 |
| WO | WO 92 03983 | 3/1992 | ............ A61C/5/14 |

* cited by examiner

Primary Examiner—Mark Bockelman
(74) Attorney, Agent, or Firm—Orrick, Herrington & Sutcliffe LLP

(57) ABSTRACT

An active implantable medical device for electrostimulation in response to a determined sleep apnea syndrome, particularly a pacemaker. This device measures the respiratory activity of the patient, using for example, a minute ventilation sensor and/or a blood oxygen saturation sensor, and analyzes the sensor signal, to determine occurrence of an apnea according to the signal delivered by the sensor. The device also delivers an increase cardiiac pacing rate in the event of detection of apnea. The device also can deliver a neurological and/or cardiac stimulation so as to apply selectively to the patient an electric stimulus. The device also determines the patients's state of activity, according to predetermined criteria, such that the increased pacing rate is provided only during a sleep phase and otherwise inhibited. The analysis can in particular detect and occurrence of successive apnea during a phase of sleep and determine the occurrence of a sleep apnea syndrome when the number of apnea events detected during a given period of time exceeds a predetermined threshold.

31 Claims, 9 Drawing Sheets

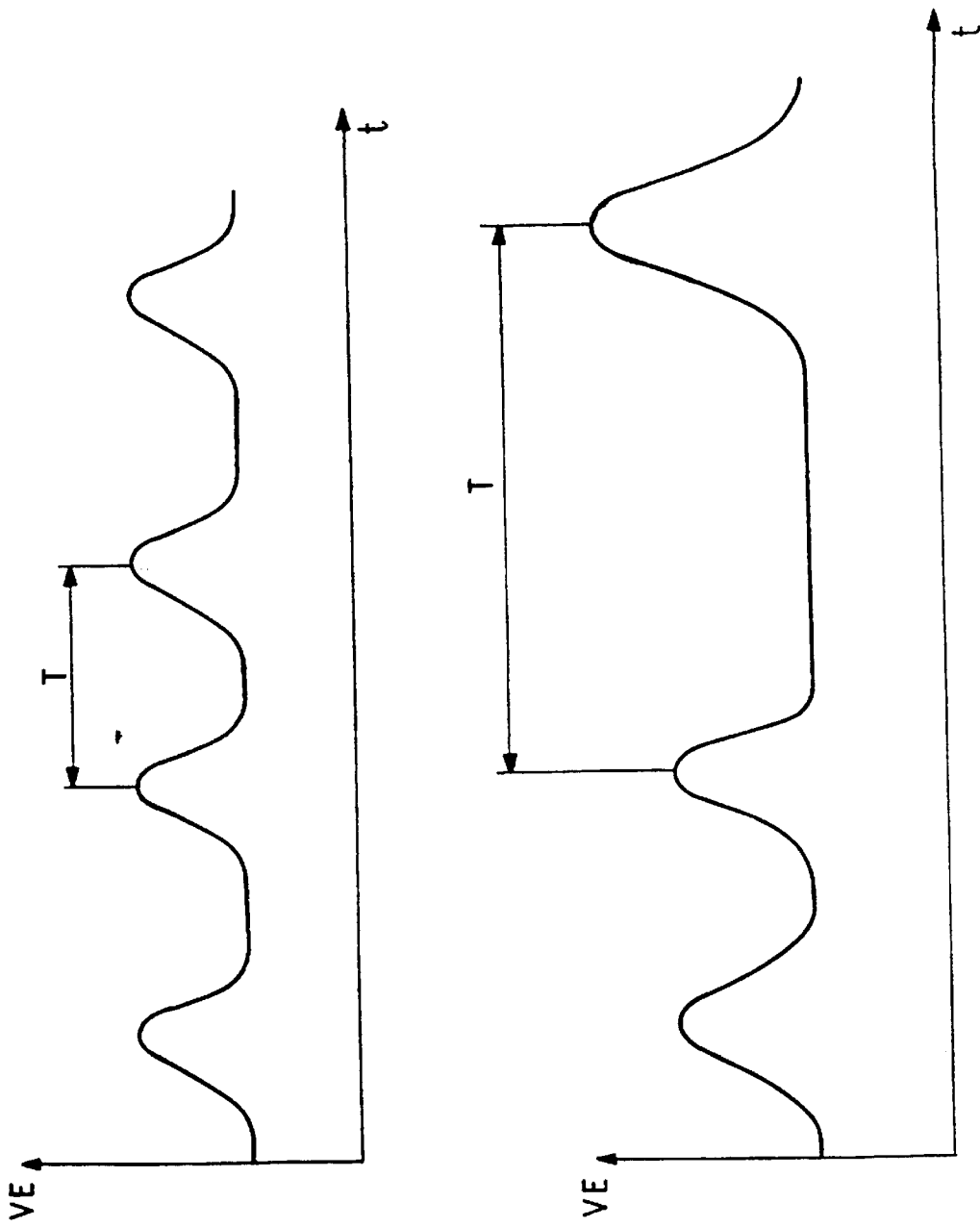

ACTIVE IMPLANTABLE MEDICAL DEVICE FOR TREATING SLEEP APNEA SYNDROME BY ELECTROSTIMULATION

FIELD OF THE INVENTION

The present invention relates to the diagnosis of the syndrome of sleep apnea and more particularly, cardiac pacemakers able to detect sleep apnea and respond to the detection with electrostimulation.

BACKGROUND OF THE INVENTION

The syndrome of sleep apnea ("SAS"), more precisely the syndrome of obstructive and non central sleep apnea ("SOAS") is an affliction having generally as its origin an obstruction of the respiratory tracts. It is likely to involve a certain number of disorders such as painful and/or insufficient breathing, an abnormal heartbeat, and hypertension. Various treatments of SAS have been proposed, including treatments involving surgery, medication, and maintenance of a positive pressure in the respiratory tract by means of a facial mask worn during sleep.

One technique, as discussed in EP-A-0 702 979 (to Medtronic) proposes to treat SAS by electrostimulation. This document describes an implanted pulse generator, controlled by a sensor, which may be a dynamic pressure sensor or a sensor of intrathoracic impedance, making it possible to follow (monitor) the patient's respiration rate and thus to detect the occurrence of an apnea. When an apnea is detected, the generator delivers a salvo (sequence) of pulses to a stimulation electrode implanted in the muscles controlling the patient's airway. This technique is not, however, in practice, completely satisfactory. This is because the stimulation which is systematically started in the event of an increase in the intratracheal pressure, whatever the cause of this increase in pressure, and whether it is due to an SAS or not, will include inappropriate stimulations.

Pacemakers having a cardiac stimulation or pacing rate which is responsive to a detected physiological or physical parameter of the patient are known. Generally, as the measured parameter increases, it reflects an increasing level of activity of the patient (e.g., exercise), and the stimulation frequency increases so that the pacing rate is controlled to simulate the action of a normal heart. Once such style of pacing device measures the patient's so-called minute ventilation (minute volume) based on a transthoracic or intrathoracic impedance measurement. An earlier style of such a pacing device measured the respiration rate, but this parameter is generally believed to be less useful as a physiological parameter because it does not represent the patient's metabolic demand (also referred to as the cardiac output requirements) during phases of increased patient activity.

In the case of cardiac pacemakers, all these systems operate to increase the frequency of stimulation pulses when one detects an increasing activity of the patient wearing the device (i.e., the patient in which the device is implanted or on which the device is carried), and to decrease this frequency to a base value in the case of a diminution of activity, particularly during phases of rest of the patient.

EP-A-0 493 222 describes a process of correlation between, on the one hand, the two extreme values $FC_{base}$ and $X_{max}$ of the range of the stimulation frequency and, on the other hand, value $X_{base}$ and $X_{max}$, which are respectively the rest value and the value of maximal activity, calculated from information collected by the sensor measuring the detected physiological or physical parameter (also called an "enslavement sensor.") This process of correlation is known under the name of "automatic calibration of the enslavement", and the document describes a process to determine the value of $X_{base}$ in the case of the utilization of the minute-ventilation as the parameter of enslavement. The value of the minute-ventilation at rest is then called $MV_{rest}$. This last value is obtained by the calculation of an average value during an interval on the order of 24 hours, including, therefore, periods of activity as well as periods of sleep of the wearer of the device.

It has been observed and recognized that, during phases of sleep, the values of $MV_{rest}$ can be more than 50% below the values of this same parameter recorded during periods when the patient is awake (i.e., conscious) and active.

Many parameters, including, but not limited to, the minute ventilation, the respiratory frequency, the saturation of oxygen in the blood, the temperature, or the acceleration have been acceptably used as parameters of enslavement for control functions. In particular, these parameters have been used in the case of cardiac pacemakers, to vary the instantaneous frequency of the cardiac stimulation according to the measured or calculated parameter.

The utilization of one or more, and more particularly several, sensors, is at the expense of an incremental energy consumption. This is due to the additional hardware circuits, the increase of which is directly associated to the enslavement parameter transducer(s) (power supply, injection of current (as in the case of minute ventilation and other sensors), production and analysis of the signal, etc.), as well as the software used to process the sensor produced signals. It is generally realized that the microprocessors or specific circuits executing the software or logic functions are typically large, energy-consuming components when they execute algorithms to process data and make decisions.

As used herein, the terms "enslavement" and "enslaved" mean the control function has a determined result or output that varies as a function of the monitored parameter. The functional relationship may be linear, non-linear, defined by an algorithm or a look-up table, and may be predetermined or self-adjusting.

In the case of cardiac pacemakers, all these enslavement systems compete to increase the stimulation pulse frequency when one detects an increasing activity of the patient, and to decrease the stimulation pulse frequency to a base or minimum frequency in case of a diminution of activity, and particularly during phases of rest of the patient.

OBJECTS AND SUMMARY OF THE INVENTION

It is, therefore, an object of the invention to propose a device for the treatment of SAS by electrostimulation.

Broadly speaking, the present invention concerns analyzing the metabolic and functional state of the patient, for applying, selectively, a stimulation for the treatment of SAS only during the phases of patient activity where an SAS is really likely to appear, and otherwise inhibiting any SAS stimulation.

One aspect of the invention is directed to a device which is an active implantable medical pacemaker device allowing for the treatment by increased cardiac electrostimulation of the sleep apnea syndrome in a patient i.e., including: means for measuring the respiratory activity of the patient; means for analyzing and determining an occurrence of an apnea in response to the measured respiratory signal; and means for delivering an SAS stimulation, controlled by the analyzing means, so as to apply selectively to the patient an increased cardiac stimulation rate in the event of a detection of an apnea. The SAS stimulation means is preferably a circuit which delivers SAS stimulation by increasing cardiac stimulation rate, and the respiratory activity measurement means may be a circuit which includes a minute ventilation sensor or a sensor which detects the oxygen saturation of the blood.

According to a preferred embodiment of the present invention, this device also includes means for determining a cardiac rate of the patient, including a rate in the absence of a determined apnea, means for determining a state of activity of the patient, this state being likely to take, according to predetermined criteria, a value representative of a state of sleep (also referred to as a rest phase) of the patient, such that the SAS stimulation means is triggerable only during a determined phase of sleep and otherwise is inhibited.

According to other various advantageous characteristics of the invention, the analyzing means detects an occurrence of a syndrome of sleep apnea when the number of apnea occurrences detected during a given period of time exceeds a predetermined threshold. In another embodiment, the determining means optionally determines a state of activity by analyzing the signal delivered by the means for measuring the respiratory activity of the patient, and/or by a separate auxiliary measurement means.

BRIEF DESCRIPTION OF THE DRAWINGS

Other features, characteristics and advantages of the present invention will appear to a person of ordinary skill in the art in view of the following description, which is made with reference to the drawings annexed, in which:

FIGS. 1 and 2 illustrate a signal representative of the respiration rate of the patient, in the absence of disorder and at the time of occurrence of an apnea respectively;

DETAILED DESCRIPTION OF THE INVENTION

Figure 3:
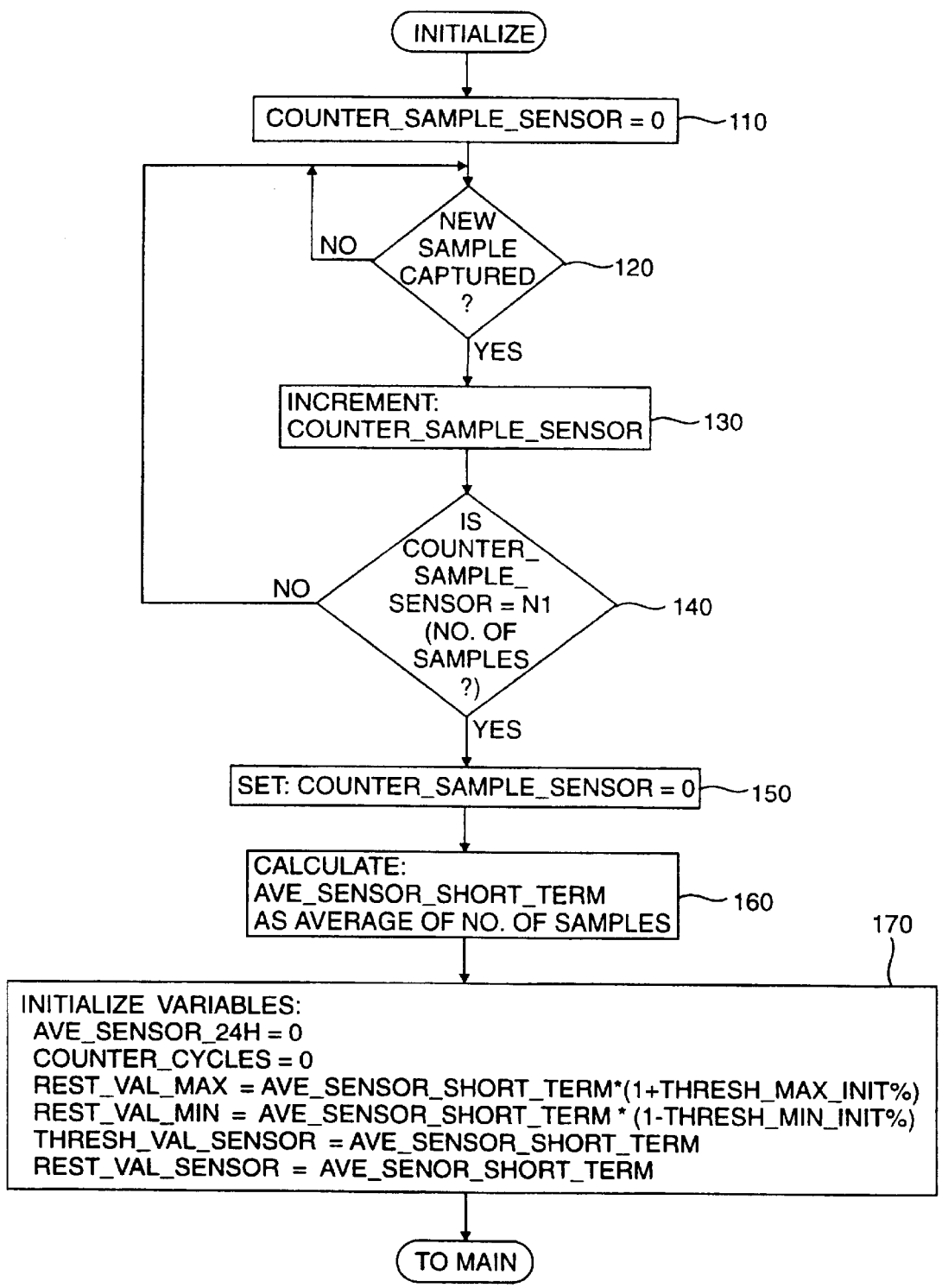
FIG. 3 is a flow chart of the initialization phase of a process in accordance with an embodiment of the invention, which may be in response to an initial operation (start-up) or a manual re-initialization as may be initiated by a therapist.

With reference to the drawing FIGS. 1 and 2, an evolution of the respiration rate of a patient during sleep is shown. It is represented by the evolution over the course of time of the minute ventilation signal (signal VE, also called signal MV), which is a parameter obtained by a measurement of intrathoracic impedance that is predominantly physiological in nature. Although the minute ventilation signal is generally easy to implement for monitoring the respiration rate of the patient, other signals coming from other types of sensors can be used in the alternative or in addition to the minute ventilation sensor, for example, a sensor measuring blood oxygen saturation.

The measurement of the minute ventilation parameters is in itself well-known. The measurement is obtained between two electrodes placed in the rib cage, or if the implanted device is a pacemaker, between an electrode (for example, a stimulation electrode) and the case of the implanted medical device. The impedance is then measured in response to an injection of a constant current of a few hundreds of microamperes, at a frequency of a few hertz, typically 8 Hz. This technique is described, for example, by J. L. Bonnet et al., "Measurement of Minute-Ventilation with Different DDDR Pacemaker Electrode Configurations", PACE, Vol. 21, 98, Part 1, and it is implemented in the commercial rate responsive pacemaker devices sold under the trademark Chorus RM 7034, by ELA Médical, Montrouge, France.

One can determine, starting from this signal, a respiratory period T (FIG. 1) which is defined as the time separating two detected impedance peaks. The peaks correspond to the high impedance obtained at the time of the inspiration (lungs being filled with air), and the decrease of the impedance corresponds to an expiratory phase.

Referring to FIG. 2, a waveform representative of a minute ventilation signal recorded among patients suffering from sleep apnea is shown. These patients have normal expiratory phases, because the pulmonary pressure is sufficient to overcome the obstruction. On the other hand, the inspiration is abnormal because the lungs cannot fill with air.

One then can observe, as illustrated in FIG. 2, an important lengthening of the respiratory period T after an expiration.

The first stage concerns diagnosing a sleep apnea occurrence. An apnea is classically defined as a respiratory pause of a duration that is greater than ten seconds, a phenomenon which is relatively easy to detect by monitoring minute ventilation. Moreover, this pause must occur during a sleep phase of the patient, because an apnea occurring while the patient is in an awake state cannot be caused by an SAS.

To respect the latter criterion, the invention proposes to discriminate between the sleep phase and the awake phase of the patient, and to apply an SAS therapy only during the sleep phase. Any treatment of an apnea which is detected during an awake phase is inhibited because, in this case, the apparent apnea normally is not pathological.

The sleep period can be diagnosed, of course, automatically, either starting from the signal delivered by the sensor monitoring the respiration activity of the patient, or by a separate sensor, for example, an activity sensor which measures a parameter which is predominantly physical such as acceleration as may be measured by an internal sensor located within the case.

EP-A-0 719 568 and its counterpart U.S. Pat. No. 5,622,428 commonly owned by ELA Medical describe in particular determining a "criterion of activity of a sensor", making it possible to make a distinction between the phases of rest (night or diurnal), and activity of the patient, in particular for contrast with a minute ventilation sensor. U.S. Pat. No. 5,622,428 is incorporated herein by reference in its entirety.

U.S. Pat. No. 5,622,428 discloses a process for distinguishing between different phases of rest of the wearer of the device, for example, rest during sleep periods and rest during awake periods, as well as other phases of activity, for example, activity during sleep and activity during awake periods and changing the operation of the device according to the detected phase.

With reference to FIG. 3, the process of the phase of initialization is illustrated. The initialization phase process broadly concerns the calculation of several variables. It is noted that the calculation of certain variables (e.g., AVE_SENSOR_24H, THRESH_VAL_SENSOR and REST_VAL_SENSOR, that will be explained in more detail below), can be undertaken according to at least two different modes, depending on whether or not the device is in an initialization phase or in the regime of normal continuous functioning, which regime is referred to as "normal functioning phase".

The phase of initialization is brought out, i.e., used, when the medical device is first placed into operation, for example, at the time of implantation, or on a specific external command (i.e., a reset function, as may be delivered telemetrically in a known manner). The initialization phase has as its purpose and objective to endow the device with an initial value that will then be automatically and subsequently redetermined over time in the normal functioning phase.

In the initialization phase, the device acquires and stores in memory a predetermined number of minute ventilation values, corresponding, typically, to 32 samples of the measure of the minute—ventilation (steps 110 to 140). Each sample corresponds to the determination of the minute—ventilation (MV) during a respiratory cycle. A counter referred to as COUNTER_SAMPLE_SENSOR is used to control the acquisition of the sample measures. The counter COUNTER_SAMPLE_SENSOR is reset to zero (step 100) at the start of the initialization phase, and increments (step 130) one count after each sample is successively acquired (step 120).

When the value of the counter COUNTER_SAMPLE_SENSOR reaches the predetermined number N1, e.g., N1=32; the counter is reset to zero (step 150) and the device then calculates an average of the 32 successively acquired values. This average is referred to as AVE_SENSOR_SHORT_TERM (step 160).

At step 170, the different variables used in the process of invention are then initialized. The counter COUNTER_CYCLES_24H and the variable AVE_SENSOR_24H are reset to 0, the variables THRESH_VAL_SENSOR and REST_VAL_SENSOR are set to the value AVE_SENSOR_SHORT_TERM that was determined at step 160. The variable REST_VAL_MAX is set to a value that is related to the determined AVE_SENSOR_SHORT_TERM by a first predetermined coefficient (1+THRESH_MAX_INIT %), typically increased by 50%, and the variable REST_VAL_MIN is set to a value that is related to the determined AVE_SENSOR_SHORT_TERM by a second predetermined coefficient (1−THRESH_MIN_INIT %), typically decreased by 50%.

These initialized variables then serve as the initial values in the normal functioning phase, which is now described with reference to FIGS. 4 to 10.

Figure 4:
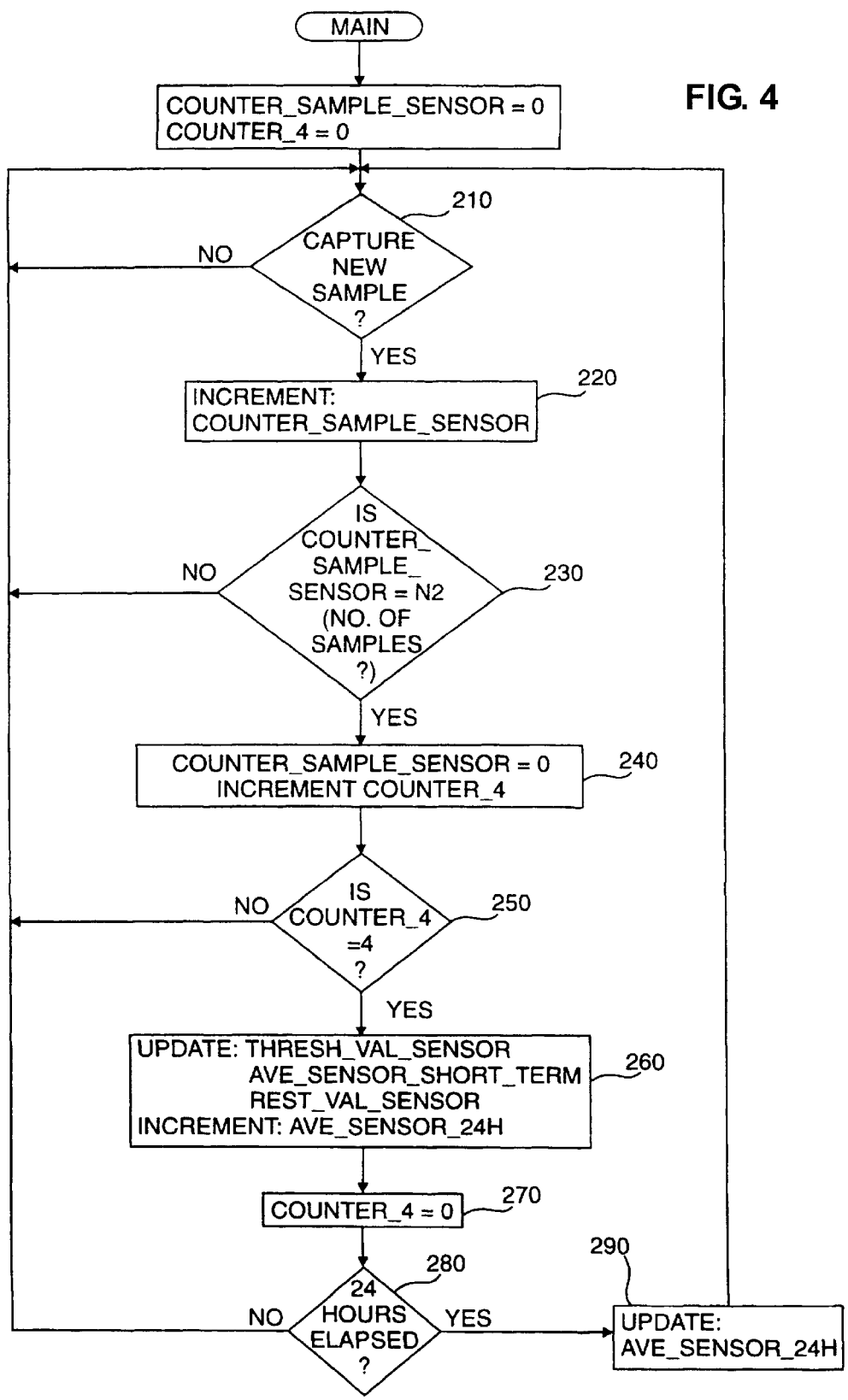
FIG. 4 is a flow chart of a normal functioning phase, during the course of which one continuously determines different variables according to the invention.

The general progress of the normal functioning phase is illustrated in a general manner in FIG. 4. The implantable device executes the following steps: At step 200, the two counters COUNTER_SAMPLE_SENSOR and COUNTER_4 are reset to zero, and in steps 210 to 250 a selected number N2 of successive samples as obtained by the sensor are collected and stored in a memory.

After 128 samples have been collected, that is to say after four repetitions of the collection of 32 samples, namely when COUNTER_SAMPLE_SENSOR=N2=32 and COUNTER_4=4 at step 250, the device then updates the variables at step 260. The variable THRESH_VAL_SENSOR is updated, in accordance with the process illustrated in the flow chart of FIG. 5. The variable AVE_SENSOR_SHORT_TERM is calculated as an average of the 128 previously measured samples (it being understood that the, numbers of 128; 32 samples and 4 cycles, are exemplary and not limiting, and each can be replaced by a different value, as appropriate for the memory of the device and its processing power). The REST_VAL_SENSOR is updated in accordance with the process illustrated in the flow chart of FIG. 6; and the variable AVE_SENSOR_24H is updated in accordance with the process illustrated in the flow chart of FIG. 7.

Figure 5:
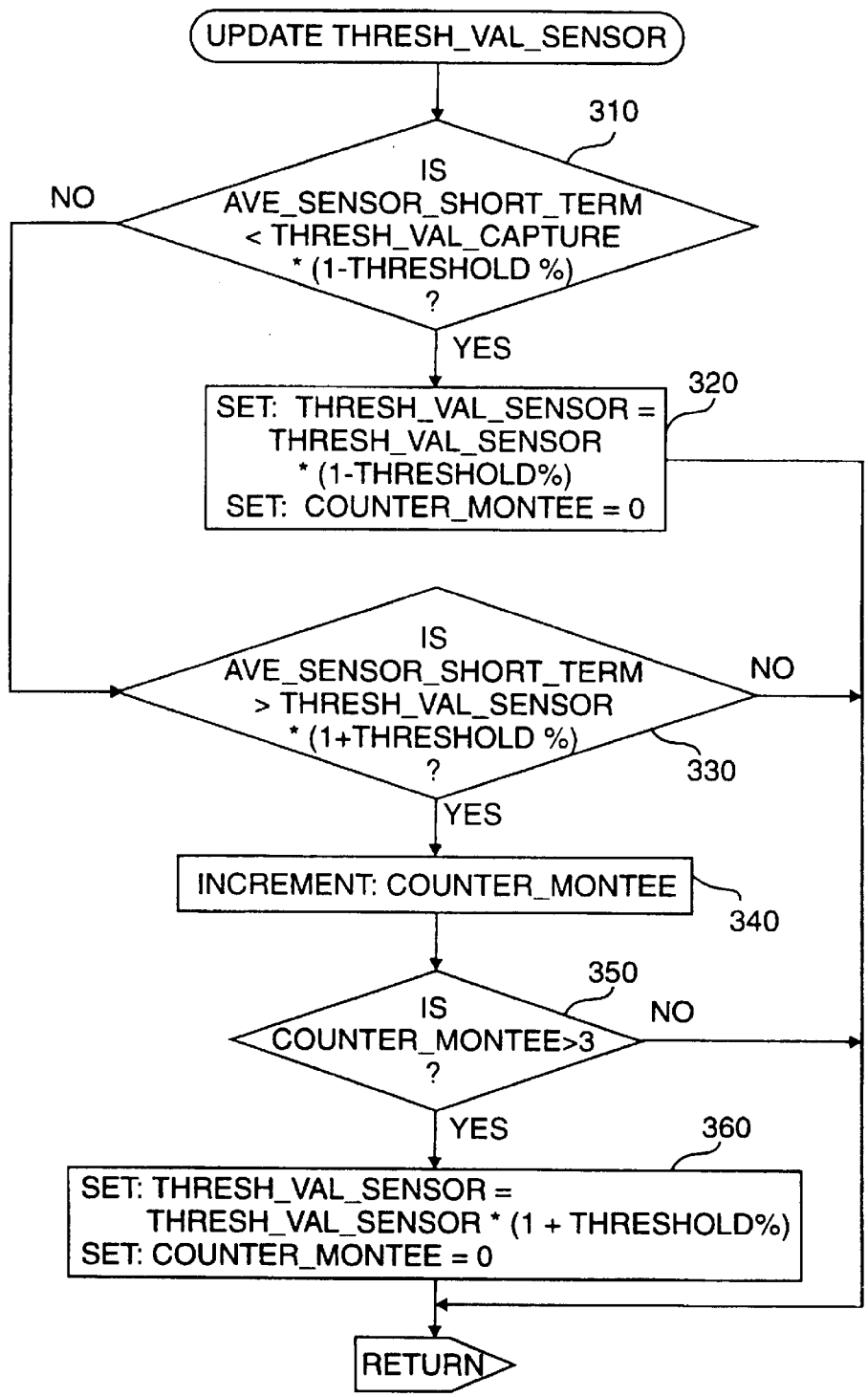
FIG. 5 is a flow chart of a process to update the variable THRESH_VAL_SENSOR of the process illustrated in FIG. 3.

Referring to FIG. 5, the periodic update of the variable THRESH_VAL_SENSOR in a preferred embodiment is described. First, this variable serves to determine the level of activity of the sensor at the end of step 260, that is to say after 128 cycles of sample measurement. It is used in addition for the calculation of variables REST_VAL_SENSOR and AVE_SENSOR_24H. It is calculated of the following manner. If the value of AVE_SENSOR_SHORT_TERM is comprised within the limits bounded by THRESH_VAL_SENSOR±THRESHOLD % (where the THRESHOLD % is a predetermined value, typically 6.25%), then THRESH_VAL_SENSOR is not modified (steps 310 and 330). If, however, the value of AVE_SENSOR_SHORT_TERM has become less than THRESH_VAL_SENSOR_THRESHOLD %, one considers that the acquired (sensed) activity level has decreased, and one decreases then the variable THRESH_VAL_SENSOR by a quantity THRESHOLD %, and resets to zero the counter COUNTER_MONTEE (steps 310 and 320), and if the value of AVE_SENSOR_SHORT_TEPM has become greater than THRESH_VAL_SENSOR+ THRESHOLD %, then one increases the counter COUNTER_MONTEE by one count (steps 310, 330 and 340).

If the counter COUNTER_MONTEE reaches a predetermined count value, e.g., 4 (a number chosen in an arbitrary manner, but corresponding to a typical situation), one considers that the sensed activity level has increased, and one increases then THRESH_VAL_SENSOR by a quantity THRESHOLD %, and resets to zero COUNTER_MONTEE (steps 350 and 360).

Figure 6:
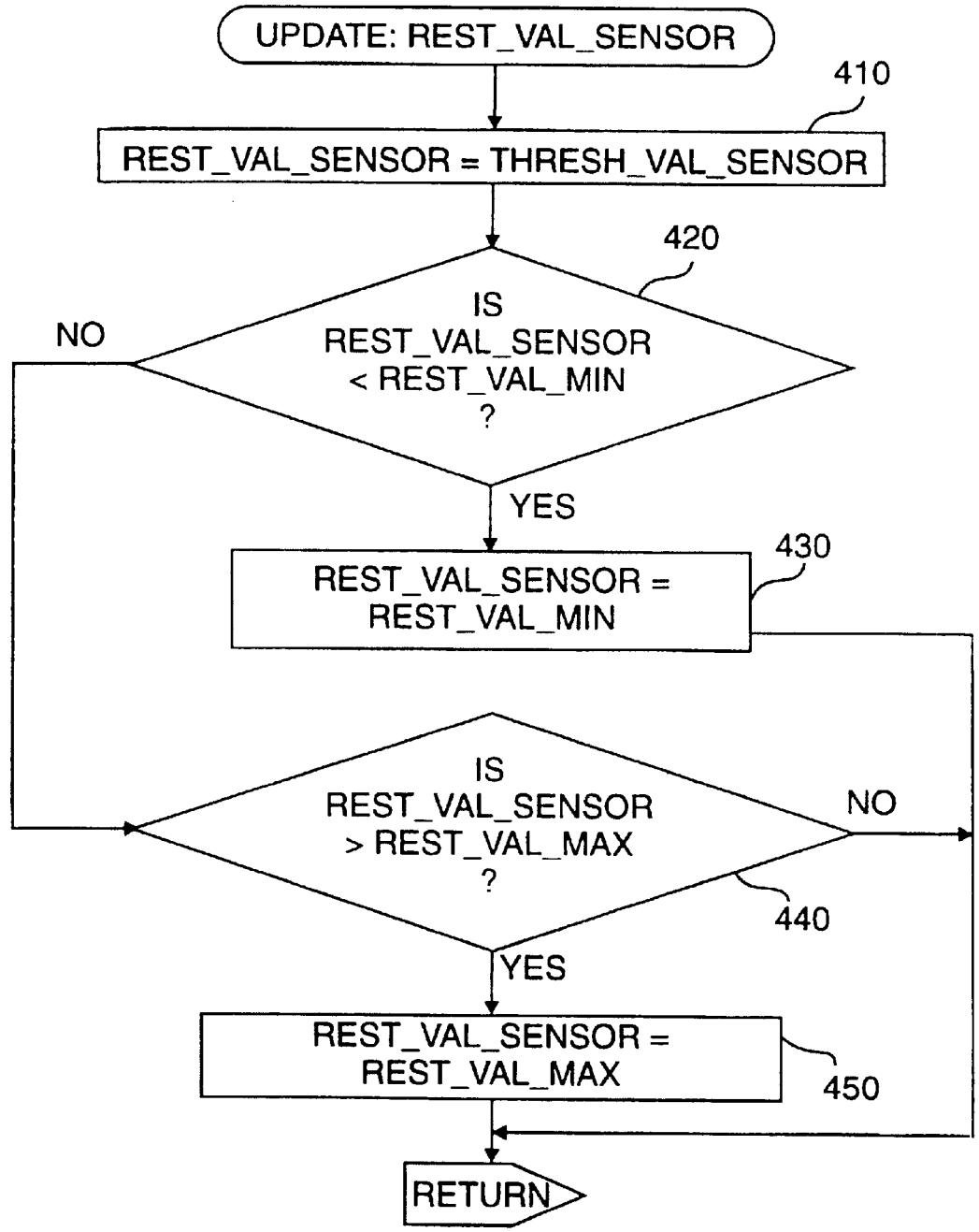
FIG. 6 is a flow chart of a process to update the variable REST_VAL_SENSOR of the process illustrated in FIG. 3.

Referring to FIG. 6, the periodic update of the variable REST_VAL_SENSOR is described. The value REST_VAL_SENSOR has a default value which is the previously deterined THRESH_VAL_SENSOR at step 410.

But REST_VAL_SENSOR is nevertheless limited to two limits depending on then the value of REST_VAL_SENSOR is set equal to the value of REST_VAL_MIN (steps 420 and 430); If REST_VAL_SENSOR is greater than REST_VAL_MAX, then the value of REST_VAL_SENSOR is set equal to the value REST_VAL_MAX (steps 420, 440 and 450). The determination of the values REST_VAL_MIN and REST_VAL_MAX are explained hereafter, with reference to FIG. 8, especially in the case where these values do not correspond to those established during the initialization phase (step 170).

Figure 7:
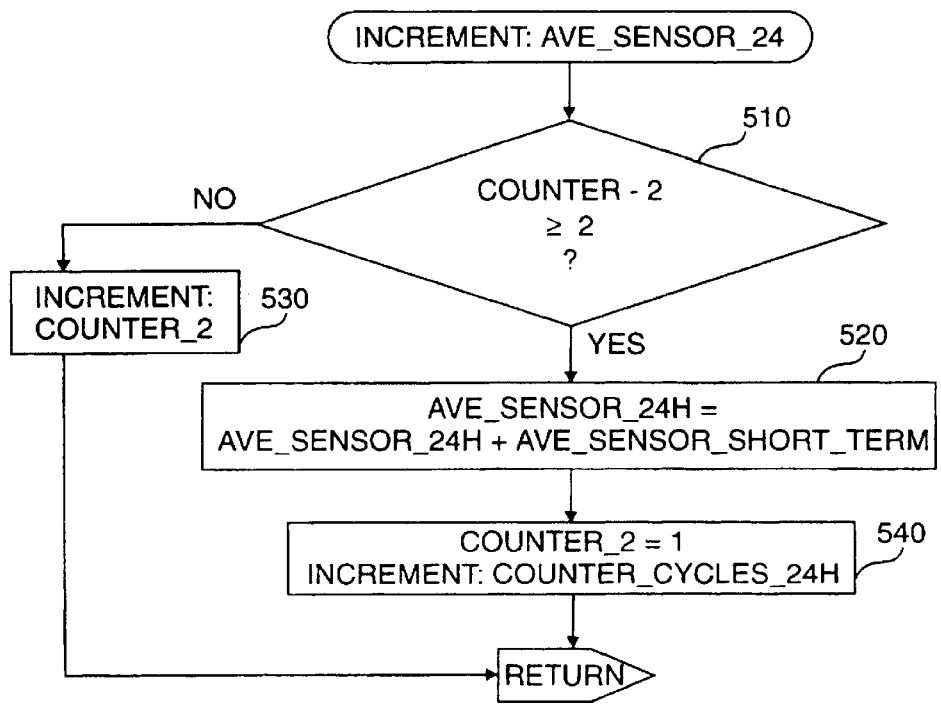
FIG. 7 is a flow chart of a process to increment the variable AVE_SENSOR_24H of the process illustrated in FIG. 3.
Figure 8:
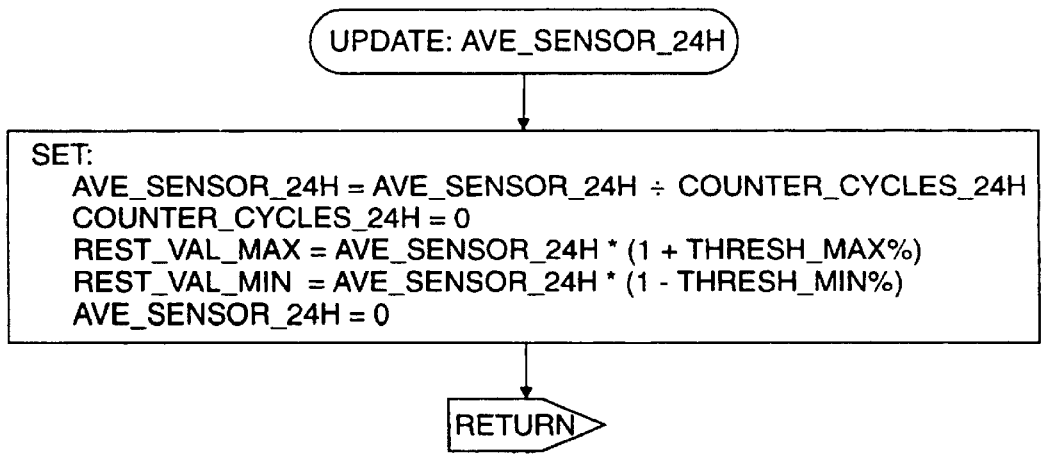
FIG. 8 is a flow chart of a process to update the variable AVE_SENSOR_24H of the process illustrated in FIG. 3.

Referring to FIGS. 7 and 8, the determination of the variable AVE_SENSOR_24H is described. This variable is first incremented in manner specified on the flow chart of FIG. 7, which is implemented during the course of step 260 of the process shown in FIG. 4. Following the value of COUNTER_2 (a counter that can have only two values, e.g., 1 or 2), one increases the variable AVE_SENSOR_24H by the value of AVE_SENSOR_SHORT_TERM at step 520, and one increments a counter COUNTER_CYCLES_24H at step 540.

At the end of a period of 24 hours (step 280 of FIG. 4), which is calculated from either an internal clock signal of the device or from a number of iterations of preceding phases corresponding approximately to a duration of 24 hours, the device updates the variable AVE_SENSOR_24H (step 290 of FIG. 4).

The different operations resulting in this update of AVE_SENSOR_24H are clarified in step 610 of FIG. 8. More precisely, the variable AVE_SENSOR_24H takes the value of the average of the sum of AVE_SENSOR_24H established at step 520, an average that is calculated by dividing the total of the sum by the value COUNTER_CYCLES_24H determined at step 540, as described above (FIG. 7).

At step. 610 (FIG. 8), the device then sets the values REST_VAL_MAX and REST_VAL_MIN, calculated from preceding result by the value AVE_SENSOR_24H. The maximal value, REST_VAL_MAX, of the REST_VALUE range, is set equal to AVE_SENSOR_24H×(1+THRESH MAX %), typically THRESH_MAX is a predetermined value, e.g. 50%. The minimal value, REST_VAL_MIN, of the REST_VALUE range is set equal to AVE_SENSOR_24H×(1−THRESH_MIN %). Typically THRESH_MIN % is a predetermined value and may be, e.g., 0.

At the end of the step 610, AVE_SENSOR_24H and COUNTER_CYCLES_24H are initialized to zero.

One will note that the determination of the variable REST_VALUE, in combination with the two extreme variation boundary limits REST_VAL_MAX and REST_VAL_MIN (themselves dependent on the variable AVE_SENSOR_24H) allows to establish, in a manner perfectly appropriate, the low point of the automatic calibration curve of the enslavement function that is described in the aforementioned EP-A-0 493 222, which is incorporated herein by reference, where one will be able to make correspond to define a relationship between REST_VALUE and the frequency of stimulation $Fc_{base}$ programmed by the therapist.

Figure 9:
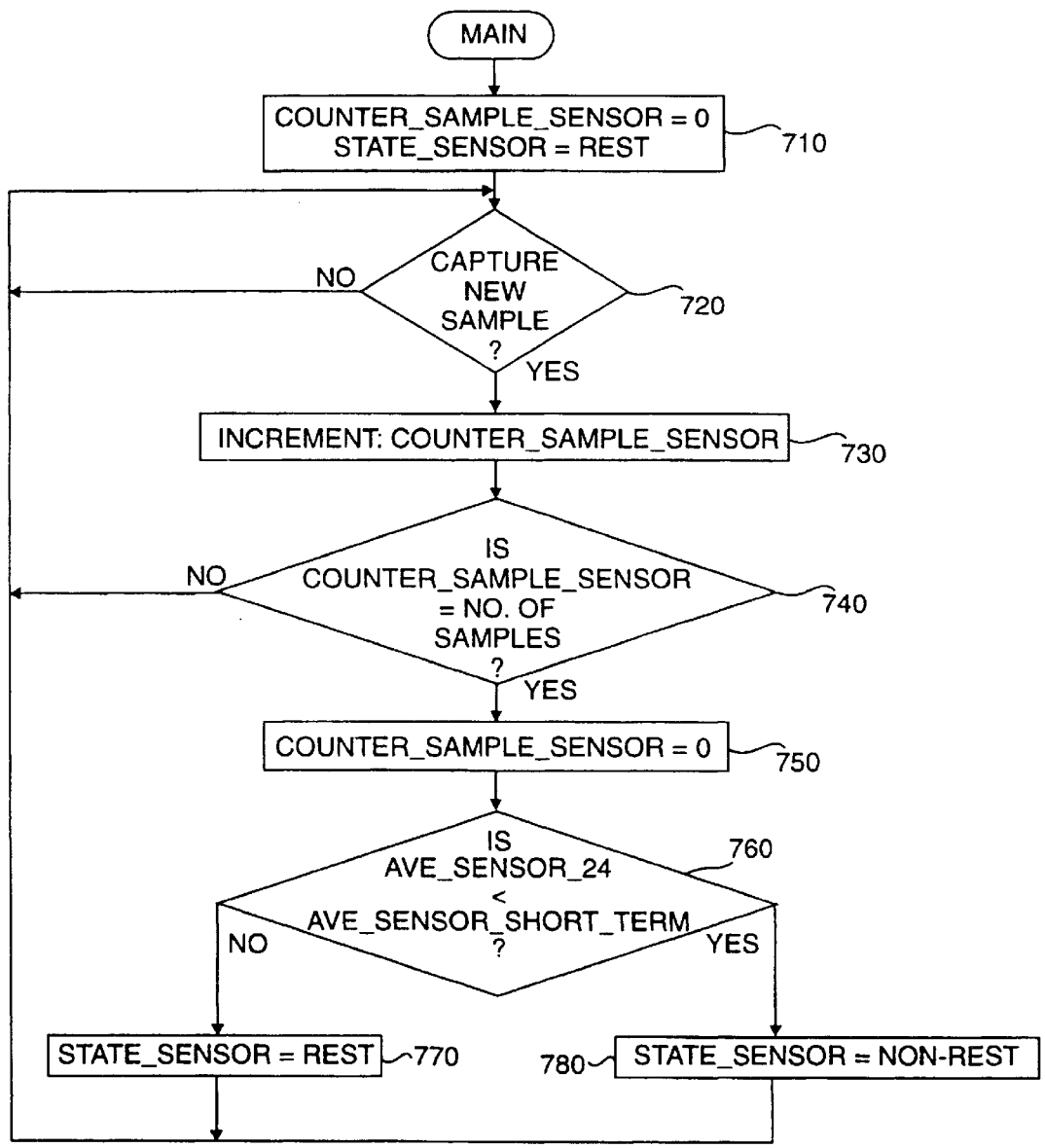
FIG. 9 is a flow chart of a process to determine the variable STATE_SENSOR in the case of the utilization of a physiological parameter (ventilation—minute, temperature, etc.)
Figure 10:
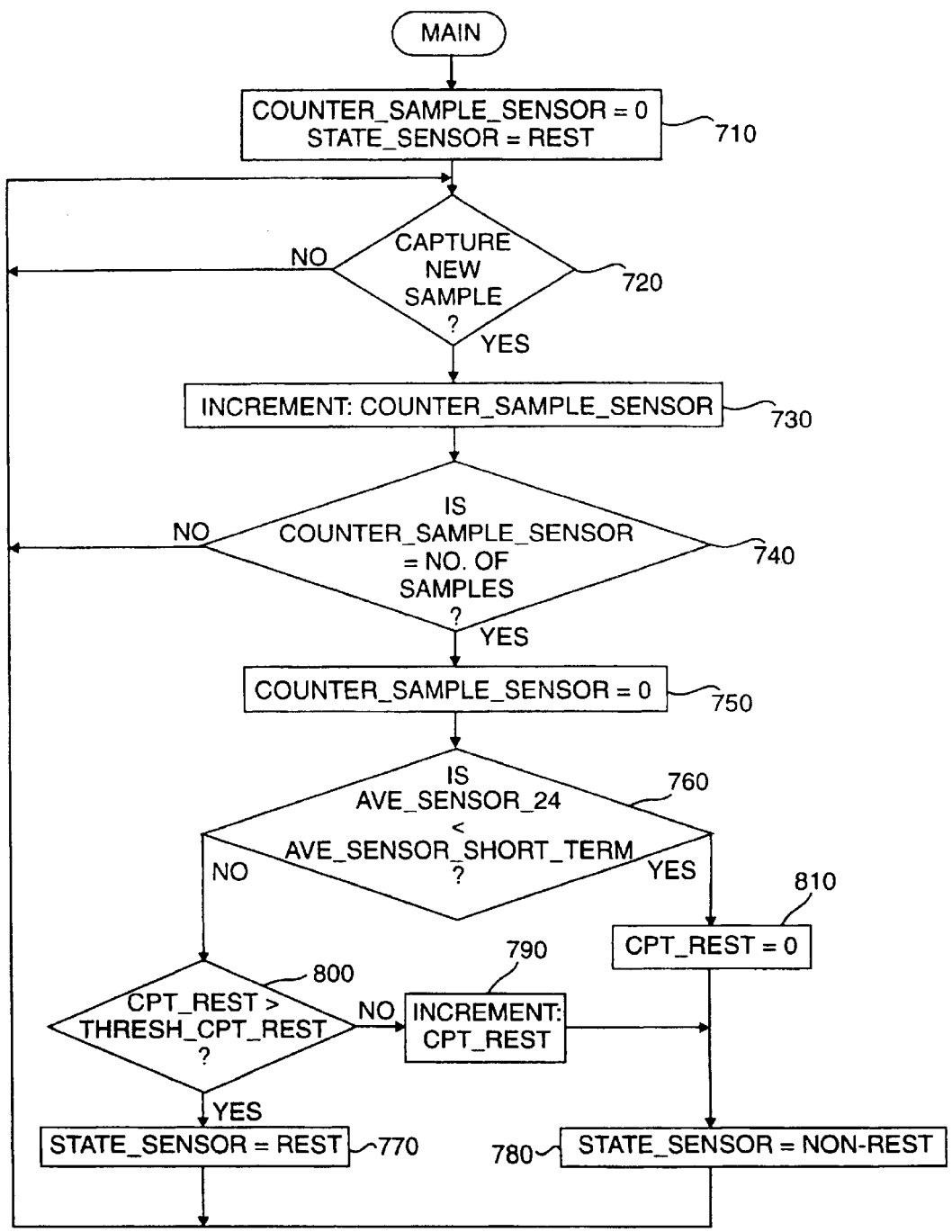
FIG. 10 is a flow chart of a process to determine the variable STATE_SENSOR in the case of the utilization of a non-physiological parameter such as acceleration.

The "criterion of sensor activity" defined above, corresponding in a variable STATE_SENSOR, is determined in accordance with the flow chart illustrated in FIGS. 9 or 10, depending on the type of enslavement sensor used.

After a phase of initialization (step 710) and after a number of cycles corresponding to the value of COUNTER_SAMPLE_SENSOR, that is, typically after 32 cycles (steps 720 to 750), the device compares the variable AVE_SENSOR_24H and AVE_SENSOR_SHORT_TERM (step 760). If AVE_SENSOR_SHORT_TERM is less than AVE_SENSOR_24H, the device considers that the average level of activity for that period is below the average level of activity over a period 24 hours, and, therefore, the patient is reliably determined to be in a proven rest state (for example, a nocturnal sleep phase). The device then sets the value of STATE_SENSOR to "Rest" (step 770). In the opposite case, it considers that there is no rest, that the patient is alert and active, and sets the value of STATE_SENSOR to "Non-Rest" (step 780).

For a non-physiological sensor (for example, a sensor of acceleration), the flow chart of FIG. 9 is slightly modified, as in the manner illustrated in FIG. 10. In this case, a counter CPT_REST is employed; it is reset to zero at the initial step 710 and incremented (step 790) each time that the device determines that the patient is in a proven state of rest. If this situation repeats a predetermined number of times, designated $THRESH\_CPT_{13}$ REST, typically on the order 12 repetitions during the 24 hour period (step 800), then the value of STATE_SENSOR is set to "Rest" (step 770). In the opposite case, one re-initializes CPT_REST to 0 (step 810) and sets STATE_SENSOR to "Non-Rest" (step 780). One will note incidentally that the flow chart of FIG. 9 corresponds in fact to a simplified version of that of FIG. 10, with THRESH_CPT_REST=0.

In an alternative embodiment, one can replace the counter incrementation and the test of the number of occurrences of samples acquired, by a test conducted over a fixed period defined by the internal clock of the device, for example, a fixed period of 10 minutes can be used to acquire the data used to calculate the short term average.

Figure 11:
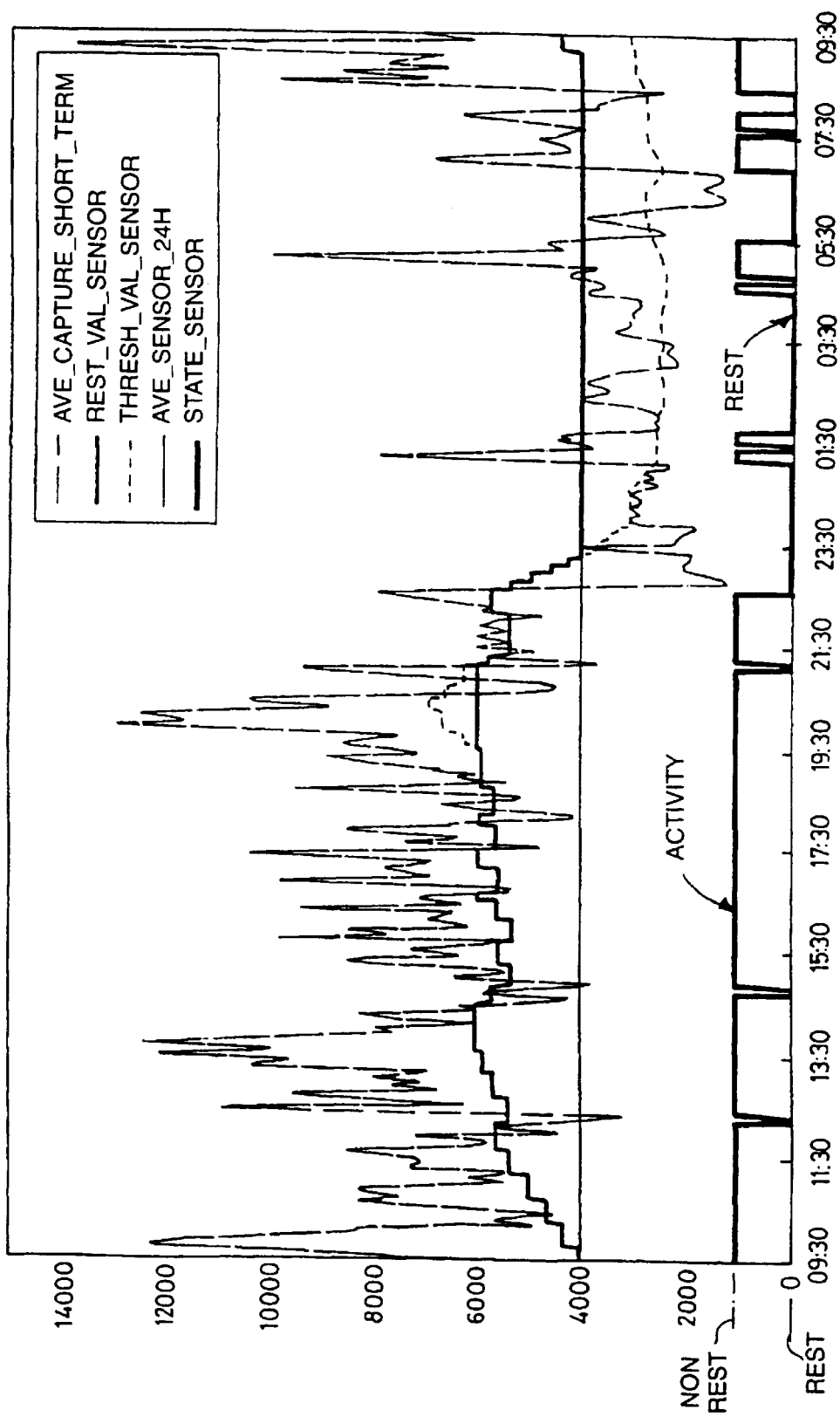
FIG. 11 is an illustration showing the evolution over time of the different variables of the process of the invention, recorded during an exemplary 24 hour time interval.

FIG. 11 illustrates an example of the evolution of the different variables THRESH_VAL_SENSOR, AVE_SENSOR_SHORT_TERM, REST_VAL_SENSOR and AVE_SENSOR_24H, over a 24 hour period as well as of the activity criterion STATE_SENSOR determined accordingly to the process of the invention. One can note that, during the phase of sleep between 23:00 hours (11:00 pm) and 6:00 hours (6:00 am), the variable STATE_SENSOR is preponderantly set to the state "Rest", and includes Non-Rest states.

The information given by the variable STATE_SENSOR thus will be able to be used by the device to trigger various functions necessitating or exploiting the knowledge of the Rest phases of the wearer of the device. It will be appreciated that by the use of additional thresholds, averages, and coefficients, multiple states of relative rest and activity may be defined for use by the device.

The EP-A-0 750 920 and its counterpart U.S. Pat. No. 5,722,996 and EPA-0 770 407 and its counterpart U.S. Pat. No. 5,766,228 both commonly assigned to ELA Medical, describe medical devices using combined information of a physiological sensor and a physical sensor, in particular a minute ventilation sensor and an accelerometer, to determine a state of a activity or a state of rest of the patient. U.S. Pat. Nos. 5,722,996 and 5,766,228 are incorporated herein by reference in their entirety.

Thus, having diagnosed an apnea, and having confirmed that this apnea is a sleep apnea, one then can carry out a calculation of an index of apnea. In this regard, when the apnea index exceeds a predetermined threshold, for example, more than ten apnea occurrences per hour (this threshold number can, of course, be programmable to be suitable for the particular patient), the presence of an SAS is determined. As soon as an SAS is diagnosed, an electric stimulation is then applied to the patient to compensate for the harmful effects of the SAS.

The electric stimulation can be a muscular stimulation (as described, for example, in the EP-A-0 702979 mentioned above or a neurological stimulation, to cause the immediate opening of the esophagus in order to allow inspiration. In the latter case, a neurological stimulation preferably will be applied only during the inspiratory phases of the patient's breathing cycle so as not to disturb the expiratory phase.

One also can envisage an embodiment whereby a stimulation is delivered only if the inspiratory period exceeds a preset value, for example, six seconds.

Further, in the preferred embodiment, the electric stimulation is a cardiac stimulation, for example, to accelerate the heart rate (frequency) of the myocardium, to compensate for the effects of the SAS. Such a cardiac stimulation will be applied to as soon as an SAS is diagnosed, by increasing the stimulation frequency by a few beats per minute (typically+ 10 bpm), compared to the natural sinusal rate of the patient. The number of beats is preferably at least 10 beats higher. Such a device includes means for determining. a cardiac rate of the patient. The stimulation at the higher rate is applied for a given period of time, for example, sixty seconds and afterwards the device reverts to the former mode of operation, e.g., the lower stimulation frequency. It also should be understood that the increased cardiac stimulation can be applied together with a muscular and/or a neurological stimulation in response to a determined SAS.

A first sensing circuit determines a state of activity of the patient. This determination may be made, for example, by comparing the first sensor output signals to predetermined criteria which is a calculated value representative of a patient state of activity, in which case the state of activity of the sensor is determined. Alternatively, the first sensor circuit may compare the parameter calculated from the first sensor output signals to a predetermined criteria which is a calculated value representative of a patient state of activity in which case the activity level of the patient is determined. In each case, the predetermined criteria is representative of a state of rest of the patient, such that it is used to discriminate a level of patient activity corresponding to rest from a level of activity corresponding to non-rest.

The sensing circuit comprises substantially all of logic and hardware elements required to operate the sensor to sense the parameter and produce output signals corresponding to the sensed parameter, and to deliver a signal utilizable by the main circuit of the pacemaker. The main circuit includes a microprocessor and memory (RAM and/or ROM), as well as conventional latches, registers and power supplies (not shown) for processing the information for the enslavement of the stimulation frequency.

Furthermore, the preferred embodiment of the process described herein is implemented in an architecture including a microprocessor having associated software instructions stored in memory (ROM) and analog and digital logic circuits that are themselves known. Such an architecture is, for example, employed in dual chamber cardiac pacemakers sold under the trade name CHORUS, manufactured by ELA Medical.

Although it does not present all of the advantages of the preferred solution with a microprocessor, a design in hardwired discrete circuits having dedicated logic circuits is nevertheless perfectly foreseeable, and equally within the framework of the present invention.

One skilled in the art should understand that the invention is not limited to the disclosed embodiments, which are presented for purposes of illustration and not of limitation.

I claim:

1. A cardiac stimulation device for treating the syndrome of the sleep apnea of a patient by electrostimulation comprising:
   means for measuring the respiratory activity of the patient having an output signal representative of the patient's respiratory activity;
   means for analyzing the patient's respiratory activity according to the output signal from the respiratory measuring means to determine an occurrence of an apnea;
   means for determining a cardiac rate of the patient, including a second rate in the absence of a determined apnea;
   means for stimulation, controlled by the analyzing means, to apply selectively to the patient cardiac stimuli at a first rate in the event of a detection of an apnea, said first rate being higher than the second rate;
   means for determining a state of activity of the patient, said state being selected, according to predetermined criteria, from among a first value representative of a sleep state of the patient and a second value representative of an awake state of the patient;
   wherein the stimulation means is applying to the patient cardiac stimuli at the first cardiac rate only during a determined sleep phase.

2. The device of claim 1 in which the stimulation means stimulates in response to being triggered at the first rate, wherein the first rate is at least 10 beats higher than the second rate.

3. The device of claim 1, in which the analyzing means detects an occurrence of successive apnea during a sleep phase and determines an occurrence of a syndrome of apnea of the sleep when the number of apnea detected during a given period of time exceeds a predetermined threshold.

4. The device of claim 1, in which the means of determination of a state of activity further comprises analyzing the output signal from said measuring means.

5. The device of claim 1, further comprising an auxiliary measuring means for measuring a state of activity of the patient; wherein the means for determining the state of activity further comprises means for analyzing the output signal from the auxiliary measuring means, said auxiliary measuring means output signal being distinct from said means for measuring of the respiratory activity of the patient.

6. The device of claim 1, further comprising an auxiliary means for measuring a state of activity of the patient, wherein said auxiliary measuring means further comprises an accelerometer.

7. The device of claim 1, wherein the means for measuring the respiratory activity of the patient further comprises a minute ventilation sensor.

8. The device of claim 1, wherein the means for measuring the respiratory activity of the patient further comprises a sensor of oxygen saturation of blood.

9. A cardiac stimulation device for treating a sleep apnea syndrome of a patient by electrostimulation comprising:
   means for determining a state of activity of the patient, said state being selected, according to predetermined criteria, from among a first value representative of a sleep state of the patient and a second value representative of an awake state of the patient;
   means for measuring the respiratory activity of the patient;
   means for determining an occurrence of an apnea based upon said measured respiratory activity;
   means for determining a cardiac rate of the patient during an identified sleep state as a second rate;
   means for providing a first rate for cardiac stimulation as the second rate incremented by a first number of beats per minute; and
   means for selectively applying cardiac stimulation at said first rate to the patient in response to a determined apnea during a sleep state.

10. The device of claim 9 wherein the first number of beats is at least 10 beats per minute.

11. The device of claim 10 wherein the first number of beats is 10 beats per minute.

12. The device of claim 9, wherein the apnea determining means determines an occurrence of successive apnea during a sleep phase and determines an occurrence of a syndrome of sleep apnea when the number of apnea detected during a given period of time exceeds a predetermined threshold.

13. The device of claim 9, wherein the means for determining a state of activity further comprises means for analyzing the measured respiration activity.

14. The device of claim 9, further comprising an auxiliary measuring means for measuring a state of activity of the patient having output signal; wherein the means for determining the state of activity further comprises means for analyzing the output signal from the auxiliary measuring means, said auxiliary measuring means output signal being distinct from said means for measuring of the respiratory activity of the patient.

15. The device of claim 14, wherein said auxiliary means for measuring a state of activity further comprises an accelerometer.

16. The device of claim 9, further comprising an auxiliary means for measuring a state of activity of the patient, wherein said auxiliary measuring means further comprises an accelerometer.

17. The device of claim 9, wherein the means for measuring the respiratory activity of the patient further comprises a minute ventilation sensor.

18. The device of claim 9, wherein the means for measuring the respiratory activity of the patient further comprises a sensor of oxygen saturation of blood.

19. The device of claim 9, wherein the means for selectively applying cardiac stimulation at said first rate applies said first rate for a predetermined time.

20. The device of claim 9, wherein the means for determining said second rate further comprises means for determining a natural sinusal rate of the patient.

21. A cardiac stimulation device for treating a sleep apnea syndrome of a patient by electrostimulation comprising:

a patient activity detector having predetermined criteria corresponding to a sleep state of a patient and an awake state of the patient, said detector monitoring patient activity and producing a first state output when the patient is in a sleep state and a second state output when the patient is in an awake state;

a respiratory activity monitor having a first activity output corresponding to a patient's respiratory activity;

an apnea detector responsive to said first activity output for determining an occurrence of an apnea based upon said patient respiratory activity;

a cardiac rate monitor for determining a first cardiac rate of the patient in response to the patient activity monitor producing the first state output;

a cardiac stimulator having a second cardiac stimulation rate output corresponding to the determined first cardiac rate incremented by a first number of beats per minute, said stimulator applying cardiac stimulation at said cardiac stimulation rate to the patient in response to a determined apnea and the patient activity monitor producing the first state output.

22. The device of claim 21 wherein the first number of beats is at least 10 beats per minute.

23. The device of claim 22 wherein the first number of beats is 10 beats per minute.

24. The device of claim 21, wherein the apnea detector has a predetermined count and a given time period and determines an occurrence of a syndrome of sleep apnea occurrences when the number of apnea detected while the patient activity monitor produces the first state output during the given period of time exceeds the predetermined count.

25. The device of claim 21, wherein the patient activity detector further comprises means for analyzing a respiratory activity monitor output.

26. The device of claim 21, further comprising an auxiliary patient activity monitor distinct from said respiratory activity monitor having a second activity output corresponding to a state of activity of the patient; wherein the means for determining the state of activity further comprises means for analyzing the second activity output in determining the patient's activity state.

27. The device of claim 26, wherein said auxiliary patient activity monitor further comprises an accelerometer.

28. The device of claim 21, wherein the respiratory activity monitor further comprises an electrode pair, a current injector connected in the electrode pair, a voltage detector connected to the electrode pair, and a controller operating the current injector to inject a current pulse and the voltage detector to detect a voltage in response to the current, wherein the controller calculates a minute ventilation based on the detected voltages.

29. The device of claim 21, wherein the respiratory activity monitor further comprises a sensor of oxygen saturation of blood.

30. The device of claim 21, wherein the cardiac stimulator applies cardiac stimulation at said cardiac stimulation rate for a predetermined time.

31. The device of claim 21, wherein the cardiac rate monitor determines a natural sinusal rate of the patient as said first cardiac rate.

* * * * *

UNITED STATES PATENT AND TRADEMARK OFFICE
CERTIFICATE OF CORRECTION

PATENT NO. : 6,574,507 B1
DATED : June 3, 2003
INVENTOR(S) : Jean-Luc Bonnet

It is certified that error appears in the above-identified patent and that said Letters Patent is hereby corrected as shown below:

Column 1,
Line 45, delete "Once" and insert -- one such -- therefor;

Column 3,
Line 4, after "increasing" insert -- the --;

Column 6,
Line 12, delete "the, numbers" and insert -- the numbers -- therefor;
Line 38, delete "SHORT-TEPM" and insert -- SHORT-TERM -- therefor;
Line 56, after "depending on" insert -- AVE_SENSOR_24H, such that: If REST_VAL_SENSOR is less than REST_VAL_MIN --;

Column 7,
Line 1, delete "in manner" and insert -- in the manner -- therefor;
Line 24, delete "from preceding" and insert -- from the preceding -- therefor;
Line 27, delete "THRESH MAX" and insert -- THRESH_MAX -- therefor;
Line 59, delete "period 24" and insert -- period of 24 -- therefor, Column 8,
Line 6, delete "THRESH_CPT$_{13}$ REST" and insert -- THRESH_CPT_REST -- therefor;
Line 6, delete "order 12" and insert -- order of 12 -- therefor;
Lines 23-24, delete "accordingly" and insert -- according -- therefor;

Column 9,
Line 3, delete "applied to" and insert -- applied -- therefor;
Line 7, delete "determining. a" and insert -- determining a -- therefor.

Signed and Sealed this

Third Day of May, 2005

JON W. DUDAS
*Director of the United States Patent and Trademark Office*